United States Patent
Kaafarani et al.

(10) Patent No.: US 6,871,783 B2
(45) Date of Patent: Mar. 29, 2005

(54) METHOD OF DISPENSING MEDICAL PRESCRIPTIONS

(76) Inventors: William Kaafarani, 7630 Horger, Dearborn, MI (US) 48127; Mohamad Bazzi, 6200 Argyle, Dearborn, MI (US) 48126

(*) Notice: Subject to any disclaimer, the term of this patent is extended or adjusted under 35 U.S.C. 154(b) by 25 days.

(21) Appl. No.: 10/650,899

(22) Filed: Aug. 28, 2003

(65) Prior Publication Data

US 2004/0078237 A1 Apr. 22, 2004

Related U.S. Application Data

(60) Provisional application No. 60/410,031, filed on Sep. 11, 2002.

(51) Int. Cl.[7] ............................................. G06F 7/08
(52) U.S. Cl. ..................................... 235/380; 235/381
(58) Field of Search .................................. 235/380, 381, 235/382, 462.01, 462.14; 705/2, 3, 4; 700/231, 232, 237

(56) References Cited

U.S. PATENT DOCUMENTS

| | | | | |
|---|---|---|---|---|
| 4,695,954 A | * | 9/1987 | Rose et al. ................. 700/236 |
| 5,845,255 A | * | 12/1998 | Mayaud ........................ 705/3 |
| 5,883,370 A | * | 3/1999 | Walker et al. ............... 235/375 |
| 6,152,364 A | * | 11/2000 | Schoonen et al. ........... 235/375 |
| 6,330,491 B1 | * | 12/2001 | Lion ........................... 700/237 |
| 6,352,200 B1 | * | 3/2002 | Schoonen et al. ........... 235/375 |
| 6,421,650 B1 | * | 7/2002 | Goetz et al. .................... 705/3 |
| 6,438,451 B1 | * | 8/2002 | Lion ........................... 700/237 |
| 6,493,427 B1 | * | 12/2002 | Kobylevsky et al. ....... 379/67.1 |
| 6,529,801 B1 | * | 3/2003 | Rosenblum .................. 700/237 |
| 6,561,977 B2 | * | 5/2003 | Williams et al. ............. 235/375 |
| 6,564,121 B1 | * | 5/2003 | Wallace et al. .............. 700/237 |
| 6,711,460 B1 | * | 3/2004 | Reese .......................... 700/237 |

\* cited by examiner

*Primary Examiner*—Thien M. Le
*Assistant Examiner*—Uyen-Chau N. Le
(74) *Attorney, Agent, or Firm*—Dinnin & Dunn, P.C.

(57) ABSTRACT

A method of dispensing medical prescriptions that includes scanning the prescription at a location remote from a dispensary, and providing an electronic communication of the prescription to the dispensary, followed by delivery or patient pick up of the prescription medicine or prescription devices. The invention further provides a process for controlling a system of processing medical prescription information that utilizes software that controls scanning of the prescription information and electronic communication of the prescription information to a dispensary. In both embodiments, the patient controls the steps in prescription filling, preferably including entry of the prescription information.

20 Claims, 2 Drawing Sheets

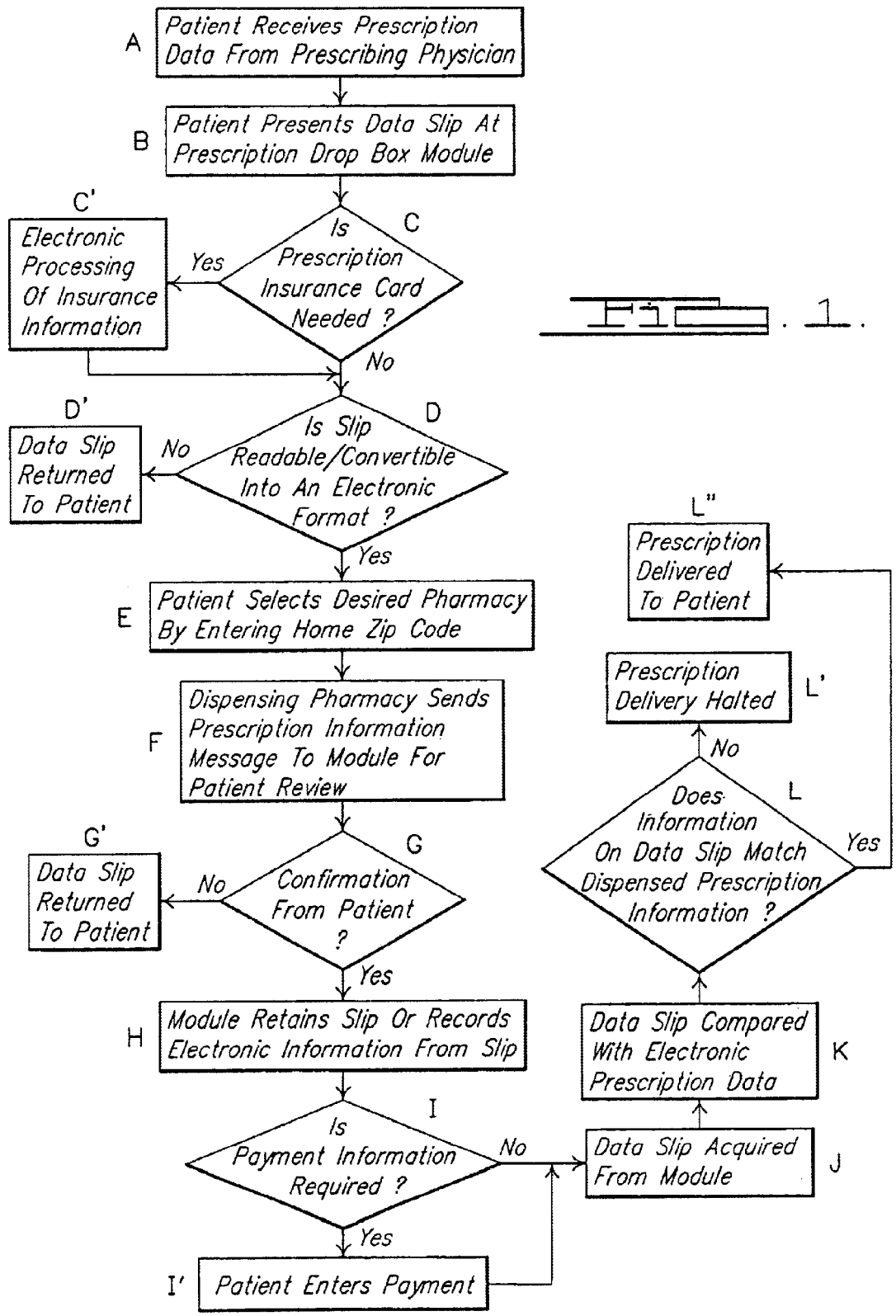

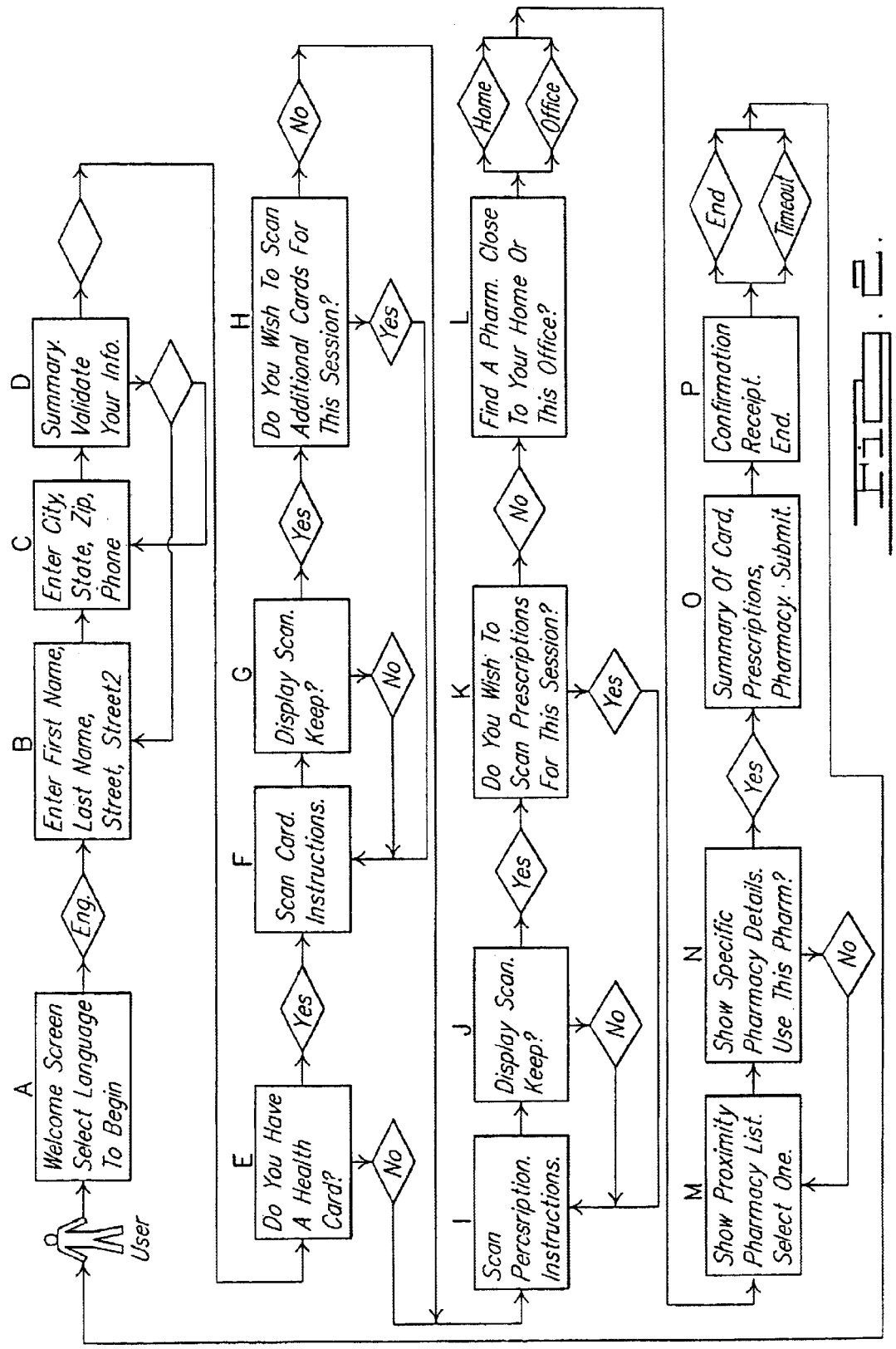

METHOD OF DISPENSING MEDICAL PRESCRIPTIONS

This Application Claims the Benefit of the Filing Date of U.S. Provisional Application Ser. No. 60/410,031, Filed Sep. 11, 2002, Hereby Incorporated by Reference in its Entirety, and is a Continuation-In-Part Thereof.

TECHNICAL FIELD

The present invention relates generally to a method of dispensing medical prescriptions, and more particularly to such a method wherein electronic prescription information is communicated from a transmitting device or machine to a remote dispensary, for delivery or pick-up by the patient. The invention is particularly applicable to streamlining the practice of medicine, reducing healthcare costs and improving patient care

BACKGROUND OF THE INVENTION

Obtaining prescription drugs and other therapeutic medical materials can require considerable time and effort on the part of the patient. In a typical scenario, the patient must obtain a written prescription from a physician or other licensed healthcare professional, take the written prescription to a registered pharmacist, then wait while the materials are prepared. While a pharmacist counts pills, checks for drug interactions, or even phones the physician or insurance carrier, the patient waits. For sick or elderly patients, travel to and waiting at the drugstore can be onerous.

In recent years, various plans have been proposed to address the problems encountered by patients in obtaining prescription materials. Prescription "vending machines" have been proposed, whereby a patient enters prescription information into a dispensing machine remote from a physician's office, as described in U.S. Pat. No. 6,529,801 to Rosenblum. While this approach may be appropriate in certain environments and for certain pharmaceuticals, inherently dangerous drugs such as prescription narcotics are ill suited for dispensing from a publicly accessible vending machine. An alternative system that attempts to facilitate dispensing of prescription drugs is set forth in U.S. Pat. No. 5,883,370 to Walker et al., hereby incorporated by reference. In Walker '370, a system is described wherein a bar coded prescription may be printed, given to a patient, and later filled at a pharmacy. Although Walker '370 may facilitate certain aspects of obtaining prescription drugs, the Walker '370 system requires computer entry of the information by someone other than the patient, for example, a healthcare professional.

Physicians write approximately 2.5 billion prescriptions a year, only about 1% of prescriptions are transmitted electronically because of security issues and viability solutions. Approximately 40% of all written drug prescriptions require rework by pharmacies. Adverse drug events (ADE) have caused 20% of the deaths in hospitals in 1999. ADE's are known to decline when physicians electronically prescribe medication, however, the time required by physicians in entering prescriptions is costly and time consuming. Moreover, the writing of prescriptions by unauthorized persons continues to be a problem as the current systems are easily duplicated. These shortcomings have contributed to rising health care and drug prescription costs.

U.S. Pat. No. 5,845,255, issued to Mayaud, hereby incorporated by reference, discloses a wirelessly deployable, computerized prescription management system consisting of creating electronic prescriptions accordance with patient-condition objectives, patient record assembly, privacy/security passwords and numeric codes for identifying patients and doctors, online access to comprehensive drug information and onscreen physician-to-pharmacy and physician-to-physician e-mail.

U.S. Pat. No. 6,493,427 to Kobylevsky et al., hereby incorporated by reference, provides a remote prescription refill system. Kobylevsky discloses one method of facilitating prescription delivery, but is limited to refills.

BRIEF SUMMARY OF THE INVENTION

It is an object of the present invention to provide a method of efficiently processing medical prescription information, and conveniently supplying prescription drugs and related goods to the patient.

It is a further object of the present invention to provide a modular device housing the physical components necessary for carrying out the above process.

It is a further object of the present invention to provide a means for educating a patient about prescription information.

In accordance with the foregoing and other objects, the present invention provides a method of dispensing medical prescriptions preferably comprising the step of providing an electronic prescription entry system remote from the prescription center and connected with an electronic communications network. The entry system preferably comprises means for converting written prescription information into electronic prescription information and means for communicating same to a plurality of remote dispensing centers. The entry system further comprises a display screen. The method further preferably includes the steps of providing to the entry system written prescription information, and providing a listing of remote dispensing centers on the display screen. The method further preferably includes the steps of communicating the electronic prescription information to a selected remote dispensing center, and generating a delivery order at the remote dispensing center. The method further preferably includes the step of receiving validating information from the written prescription information at the entry system.

FIG. 1: An illustrative, but not limiting embodiment of a method of processing data and dispensing medical prescriptions according to the present invention is set forth in a representative flow chart.

FIG. 2: Another embodiment of the present invention setting forth process steps wherein a software control system is used to control processing of data relating to a prescription filling method.

DETAILED DESCRIPTION

The present invention broadly provides a method for processing patient prescription information, and related methods for controlling a prescription information processing system, preferably having software and hardware housed in a modular kiosk. An illustrative, but not limiting embodiment of a method of processing data and dispensing medical prescriptions according to the present invention is set forth in a representative flow chart, included herewith and labeled FIG. 1. It should be appreciated that while FIG. 1 discloses one preferred embodiment of the present invention, various steps might be added to the FIG. 1 embodiment without departing from the scope of the present invention. Similarly, steps might be omitted, or the disclosed steps altered. In a further aspect, the present invention includes a modular device, hereafter the "module," housing the electronic and non-electronic hardware and software components needed for processing prescription information according to the present invention. For instance, the module preferably includes at least a computer with a display screen, a scanning device, a transmitting device, a keypad and/or a touchscreen, and a printer. In a still further aspect, the present invention provides a software, server or hardware controlled method of processing prescriptions and related information.

After a person, the "patient," has received a written prescription, hereafter "data slip," from the prescribing medical practitioner, the method of the present invention preferably begins with initial steps of converting the prescription data into an electronic format, as shown in Boxes A–D' of FIG. 1. It should be appreciated that prescription data relating to all forms of medical-related goods may be processed, and the goods delivered according to the present invention, the processing and delivery being facilitated by the modular unit including the necessary hardware and software. For example, delivery and processing of related information for prescription pharmaceuticals, diabetic supplies including hypodermic needles, and other devices and materials is contemplated. In a preferred embodiment, the module is located near a doctor or dentist's office, clinic, hospital, or other medical-related facility at which patients receive prescription data. It is contemplated that the module will be placed at a point readily accessible to persons exiting the medical facility. Alternative embodiments are contemplated wherein the module is actually placed in or near a pharmacy, and patients can deposit their prescription data for home delivery of the goods rather than waiting in line for a pharmacist to fill their order.

As shown in Box C, the presently disclosed method preferably includes the step of querying the patient for insurance information. This step preferably takes place by displaying to the patient options to proceed by either entering insurance information, or choosing not to enter insurance information, as shown in Boxes C and C'. It should be appreciated that the patient may be queried for insurance information at any point during the presently disclosed process, for example, in Boxes C and C', or prior to confirming and completing the transaction. As used herein, the term "insurance information" should be understood to include virtually any numerical or other coded identifier suitable for identifying a particular patient, insurance company, policy number or group number. Once such information is entered, which can be by way of a magnetic stripe card or similar device, the method proceeds to Box C', and the prescription information is communicated to the pharmacy and/or insurance company electronically, as shown in Box C'. The method then proceeds to Box D, where the module hardware and software preferably assess whether the data slip is convertible into an electronic format. If the patient chooses to forego processing of insurance information, the method proceeds directly to Box D from Box C.

The patient preferably places the paper on which the data are written in or on the module, as shown in Box B. The module preferably includes a facsimile, scanner, digital camera, or some other electronic device capable of converting the information on the data slip into an electronic format. If the slip is unreadable or otherwise cannot be converted into an electronic format, the data slip is returned to the patient, as shown in Box D'. Conversion to any known electronic format is possible, digital or analog, provided the information can be subsequently transmitted to a remote receiver, for example, a second facsimile machine or a computer, in a conventional manner. The remote receiver is located at a pharmacy or other prescription "dispensary," from which prescription deliveries are dispatched, or prepared for patient pickup, as described below. Transmission may occur via any known medium, for instance, telephone lines, power lines, wireless communication, etc. An internet-based means of communication is preferred, however, alternative systems/protocols might be used without departing from the scope of the present invention. Identification of the patient as the party ordering the prescription may be achieved by scanning the patient's driver's license or other ID card along with the data slip. For instance, a smart card reader, well known in the art, can be utilized with the present invention to read "Smart Cards," plastic cards imprinted with magnetic or electronic information relating to patient identification, prescription and/or medical history, other prescriptions. One suitable apparatus is set forth in U.S. Pat. No. 6,561,977 to Williams et al., hereby incorporated by reference. Similarly, thumbprints, retina patterns, or other identifying criteria could be scanned or otherwise supplied contemporaneous with processing of the prescription data. U.S. Pat. Application No. 20030028811, to Walker et al., hereby incorporated by reference, sets forth one means for utilizing a finger print scanner to facilitate prescription filling. Furthermore, bar codes, numerical identifiers, etc., may be used on the data slip itself to represent prescription or personal information. In one such embodiment, rather than transmitting an image of the data slip, representative numerical identifiers for the patient name, age, other medications, as well as the prescription information, can be transmitted to the dispensary. Prescription pads specific to the presently disclosed invention, for example having bar code or even magnetic data printed thereon, as well as logos, names, etc., are preferably supplied to the prescribing medical practitioners, allowing electronic and/or internet based tracking of each individual slip or prescription written.

Once the information is collected and transmitted, an optional step of storing the data slip itself may be undertaken, as shown in Box H. In particular, the scanner, facsimile, etc. can deposit the data slip in a locked receptacle, for later confirmation and/or analysis of order accuracy. In one contemplated embodiment, the patient deposits the data slip into a facsimile machine in a conventional manner. After "reading" the data slip, and transmitting an electronic copy of the information, the machine feeds the data slip into an inaccessible storage box located under or adjacent the module. A scanner might be used similarly. An operator or technician preferably periodically collects the data slips, and compares the slips against the prescriptions actually dispensed and delivered (described below). By storing the data slip, the present invention allows a reduction of the risk that a prescription will be filled more than once, similar to the conventional practice at pharmacies. In addition to, or instead of, storing the data slip, electronic copies of the prescription data processed or other information such as order time, cost, etc. can be stored in a computer, for later reference. Alternative embodiments, scanners, cameras, facsimiles, etc., are contemplated wherein deposit of the data slip into the storage receptacle is temporarily delayed until the transmitting machine receives a reply message confirming receipt of the order at a remote location, for instance the storage facility or pharmacy actually dispensing the delivered prescriptions. If the reply message is not received in a predetermined amount of time, the data slip can be returned to the patient for a retry or conventional prescription delivery at a pharmacy. The content of the reply message can optionally include a visually readable message (for instance, on a conventional LCD screen or other computer monitor) describing the proposed prescription delivery, as shown in Box F. If inaccurate, the patient can cancel the order by a variety of means, including pressing a key, speaking the word "No" to a voice activated system, etc. If accurate, the patient can similarly confirm the order with a keystroke, voice, etc. Alternatively, rather than retaining the slip during the ordering process, an optional series of steps is contemplated in which the order is processed and confirmed, then the prescription slip is deposited into a receptacle. Upon collecting the slips, as shown in Box J, confirmed orders can be screened for conformity therewith, as shown in Boxes K and L. If a discrepancy is found between the prescription information and the data slip, prescription delivery can be halted, as shown in Box L'.

The invention can also include steps of prompting the patient for personal information such as age, weight, home telephone number, requested delivery time, secret confirmation codes, etc., all of which can be entered electronically. A related embodiment, instead of retaining the data slip, marks the slip with indelible ink or a patterned die cut, either step providing protection against fraudulent or illegal re-use of the prescription.

Once the prescription data are received at the dispensary, the prescription is filled in a conventional manner, usually by a registered pharmacist, and can be delivered to the patient at home, work, etc. While the preferred method includes the step of delivering the prescription to the patient, this step is not critical, and the present method could include instead the step of preparing and holding the prescription for pickup by the patient. Yet another embodiment is contemplated that includes the step of sending a message to the module where the patient is located, after the prescription is prepared for either delivery or pickup. The message can include information such as prescription availability, cost, estimated delivery time, time for pickup, etc. In this and other embodiments, a printer is preferably provided which supplies a receipt or printed copy of the relevant information for the patient's use or records.

Still other embodiments are contemplated that incorporate a step of processing payment for the prescription and/or the delivery service, as shown in Boxes I and I'. For example, one variation of the present invention includes the step of providing a keypad on the module, allowing the patient to type in their insurance or other payment information for use by the dispensary. Another variation includes the step of providing a magnetic stripe reader in conjunction with an automated teller machine or credit card machine, or even a cash acceptor such as are known in the art, for example, from grocery store "U-scans." In these embodiments, the patient is able to pay for his or her prescriptions and/or for the delivery service contemporaneous with their ordering of the prescription.

Thus, the present invention provides an efficient, reliable, and cost-effective means for processing data relating to prescription drugs and related goods, and a means for facilitating delivery thereof. In particular, by focusing on actions of the patient, the time requirements previously required of pharmacists are reduced. Moreover, embodiments are contemplated (as shown in FIG. 1), wherein the step of entering a home or delivery zip code is required of the patient, as shown in box E. In such an embodiment, the patient can select the appropriate pharmacy and delivery of the prescription goods can be made from the selected dispensary, further enhancing the efficiency of the process. Still further embodiments provide the patient an optional step of dialing direct from the module to speak with a customer service representative or, if necessary, to speak with a pharmacist or pharmacy technician.

Referring now to FIG. 2, there is shown yet another embodiment of the present invention setting forth process steps wherein a software control system is used to control processing of data relating to a prescription filling method. The process set forth in FIG. 2 preferably begins by displaying at a module similar to modules described above a welcome screen to a patient, and querying the patient in what language to run the process, as set forth in Box A. For example, the patient will select English, and the process proceeds to Box B, wherein the patient is prompted to enter his first name, last name, and street address. After entering information at Box B, the process preferably continues to Box C, wherein the patient is prompted to enter his City, State, Zip Code and telephone number. After entry thereof, the process proceeds to Box D, wherein the module is directed to display on the module display screen a summary of the patient information, and the patient is queried whether the information is correct. If the patient indicates that the information is incorrect, the process returns to Box B. If the patient validates the information, the process proceeds to Box E, where the patient is queried whether he has a "health card." If the patient indicates that he does not have a health card, the process proceeds to Box I. If the patient indicates that he does have a health card, the process proceeds to Box F, wherein the patient is prompted to scan his health card. As used herein, the term "scan" should be understood to encompass any means for entering the desired prescription information electronically, such as electronically scanning data recorded in a digital or magnetic means on a card, as well as actual entry of a numerical identifier by pressing buttons on the module. Upon the patient's entry of the information, the process proceeds to Box G, wherein the module display screen displays a summary of the entered insurance information and the patient is queried whether the information is correct. If the patient indicates that the information is correct, the process proceeds to Box H. If the patient indicates that the information is incorrect, the process returns to Box F. At Box H, the patient is queried whether additional cards are to be scanned for the session. If the patient indicates that they wish to scan additional cards, the process returns to Box F. If the patient indicates that they do not wish to scan additional cards, the process proceeds to Box I.

At Box I, the patient is prompted to enter or scan the prescription information, e.g. the prescriptions themselves. After forming a preferably TIFF image of the prescriptions, although other formats such as JPEGs are contemplated, the process proceeds to Box J, wherein the module display screen displays the scanned prescriptions and the patient is queried whether the scans are acceptable. If the patient indicates that the scans are unacceptable, the process returns to Box I for re-scanning. If the patient indicates that the scans are acceptable, the process proceeds to Box K, wherein the patient is queried whether he wishes to scan additional prescriptions. If the patient indicates that no more prescriptions are to be scanned, the process proceeds to Box L. If the patient indicates that more prescriptions are to be scanned, then the process returns to Box I.

At Box L, the patient is queried whether he would like to locate a pharmacy close to his home, or to the module location itself. The patient is then offered either of an "office" or "home" option, and a proximity list is displayed on the module display screen, as shown in Box M. The patient then selects a pharmacy from the display list for either of home delivery or pick up, and the process proceeds to Box N. In Box N, the particular details of the selected pharmacy are displayed, and the patient is queried whether the selected pharmacy is acceptable. The information displayed to the patient can include availability of the particular prescription at the selected pharmacy, estimated time for pick up or delivery, cost, etc. If the patient indicates that the pharmacy is acceptable, then the process proceeds to Box O. If the patient indicates that the selected pharmacy is unacceptable, then the process returns to Box M and available pharmacies are again displayed.

In Box O, a summary of the transaction is displayed to the patient. The information displayed preferably includes any insurance information, the prescription information itself as an electronic image of the prescription or a text summary thereof, and the selected pharmacy information. The patient is prompted whether to submit the order. If the patient indicates that the order is to be submitted, then the module is directed to send an electronic order to the pharmacy via FAX, email or a similar medium. The presently disclosed software system keeps an electronic log of the transmission time, pharmacy selected, and number of pages transmitted. Upon receipt of an electronic communication from the selected pharmacy that the email, FAX, etc. has been received, a receipt is printed for the patient. If no electronic confirmation is received from the selected pharmacy within a certain pre-selected time period, the system times out and returns to the state of Box A. In a preferred embodiment, the patient presents the receipt showing the electronic log when the prescription is actually delivered of picked up, allowing confirmation and validation by the dispensing pharmacy.

It should be understood that the present description is for illustrative purposes only, and should not be construed to limit the breadth of the present invention in any way. Thus, those skilled in the art will appreciate that various modifications might be made to the presently disclosed embodiments without departing from the intended spirit and scope of the present invention.

What is claimed is:

1. A process for providing prescription products to a patient, wherein the patient is provided with prescription information from a prescription center, the process comprising the steps of:
    providing an electronic prescription entry system connected with an electronic communications network, wherein the entry system comprises means for converting written prescription information into electronic prescription information and means for communicating same to a plurality of remote dispensing centers, and wherein the entry system further comprises a display screen;
    providing to the entry system prescription information;
    providing a listing of remote dispensing centers on the display screen;
    providing an order summary comprising the prescription information on the display screen;
    communicating said electronic prescription information to a selected one of said remote dispensing centers selected by a user;
    generating a delivery order at the selected remote dispensing center; and
    receiving viewable validating information from the prescription information at the entry system.

2. The process of claim 1 further comprising the step of storing the electronic prescription information in the entry system at least temporarily.

3. The process of claim 2 wherein the entry system further includes means for reading electronic or magnetic patient medical information and means for reading electronic or magnetic patient prescription information.

4. The process of claim 3 wherein the means for reading electronic or magnetic patient medical information includes magnetic stripe reading means.

5. The process of claim 3 wherein the means for reading electronic or magnetic patient medical information includes means for reading prescription information stored in an electronic medium.

6. The process of claim 1 wherein the step of providing the prescription information comprises making the prescription information inaccessible to the patient at least temporarily.

7. The process of claim 6 wherein the step of receiving the prescription information further comprises making the prescription information temporarily inaccessible to the patient.

8. A process of electronically controlling processing of prescription information and generation of an electronic order there for comprising the steps of:
    providing an electronic user interface;
    prompting a patient via said interface to enter personal identification information and prescription information in a computer readable format;
    generating a list of suitable dispensing entities having remote receivers based on analysis of the personal identification information and prescription information, and displaying the list to the patient via the electronic user interface;
    communicating an electronic copy of the personal information and prescription information to a remote receiver selected by the patient;
    generating an electronic transaction log comprising transmission time, selected remote receiver, and number of pages transmitted to the remote receiver;
    providing a transaction confirmation to the patient in an electronic format via the electronic user interface, and prompting the patient to enter a confirmation thereof.

9. The process of claim 8 wherein the step of prompting the patient to enter personal identification information comprises prompting the patient to enter prescription drug name, quantity and refills.

10. The process of claim 8 further comprising the step of prompting the patient for entry of insurance information.

11. The process of claim 8 wherein the step of communicating the electronic copy of the personal information and prescription information to the selected remote receiver comprises communicating a TIFF image thereto.

12. The process of claim 8 wherein the step of communicating the electronic copy of the personal information and prescription information to the selected remote receiver comprises communicating text data in an electronic format.

13. The process of claim 8 wherein the process is software controlled.

14. The process of claim 8 wherein the process is hardware controlled.

15. The process of claim 8 wherein the process is server controlled.

16. A method of providing for electronic communication and validation of an order for medical prescriptions comprising the steps of:
    providing a software controlled module having a display screen, scanning means, and electronic communication means;
    generating a user prompt via said display screen for providing of patient geographic data to said scanning means;

generating a user prompt via said display screen for providing of patient prescription information to said scanning means;

generating a list of available dispensaries having remote receivers, based on synthesis of the personal identification information and prescription information, and displaying the list to a patient via the electronic user interface;

generating a user prompt via said display screen for patient selection of one dispensary;

generating a user prompt via said display screen for providing of patient insurance information to said scanning means;

providing on said display screen electronic representation of the patient prescription information, and the selected dispensary, and generating a user prompt for approval thereof;

communicating an electronic copy of the patient prescription information and the insurance information to the remote receiver of the selected dispensary via said electronic communication means;

providing on said display screen an electronic representation of order confirmation from said remote receiver;

storing in a computer readable format an electronic transaction log comprising transmission time, selected remote receiver and number of pages in the electronic copy.

17. The method of claim 16 wherein said scanning means includes a scanner for creating an electronic image of a prescription slip.

18. The method of claim 17 further comprising the step of providing marking means for indelible marking of a prescription slip.

19. The method of claim 16 further comprising the step of retaining a prescription slip in said module.

20. The method of claim 16 wherein the method is software controlled.

\* \* \* \* \*